United States Patent [19]

Fabinski

[11] Patent Number: 5,055,688
[45] Date of Patent: Oct. 8, 1991

[54] MULTICOMPONENT INFRARED GAS ANALYZER

[75] Inventor: Walter Fabinski, Kriftel, Fed. Rep. of Germany

[73] Assignee: Hartmann und Braun A.G., Frankfurt am Main, Fed. Rep. of Germany

[21] Appl. No.: 605,512

[22] Filed: Oct. 30, 1990

[30] Foreign Application Priority Data

Nov. 8, 1989 [DE] Fed. Rep. of Germany ....... 3937141

[51] Int. Cl.$^5$ ............................................ G01N 21/61
[52] U.S. Cl. ..................................... 250/344; 250/343
[58] Field of Search ................................ 250/343, 344

[56] References Cited

U.S. PATENT DOCUMENTS

| | | | |
|---|---|---|---|
| 2,898,800 | 8/1959 | Bergson | 250/344 X |
| 3,770,974 | 11/1973 | Fertig | 250/344 |
| 3,898,462 | 8/1975 | Ishida et al. | 250/344 |
| 4,336,453 | 6/1982 | Imaki et al. | 250/344 |
| 4,692,622 | 9/1987 | Taniguchi et al. | 250/344 X |

Primary Examiner—Constantine Hannaher
Assistant Examiner—Edward J. Glick
Attorney, Agent, or Firm—Ralf H. Siegemund

[57] ABSTRACT

Nondispersive infrared gas analyzer for the concurrent measurement in the concentration of several components contained in a gas sample, and including a source of and modulator for infrared radiation, a measuring and reference chamber are traversed by said beams, at least two serially pneumatic radiation detectors each having a front and a rear chamber filled with a respective component and each provided for measuring the pressure differential between the respective chambers, a filter disposed between the first detectors upstream and having opaque range which covers at least a major absorption band of the component filling the downstream detector but having a region of transparency which includes at least one secondary absorption band of that component.

4 Claims, 1 Drawing Sheet

MULTICOMPONENT INFRARED GAS ANALYZER

BACKGROUND OF THE INVENTION

The present invention relates to a nondispersive infrared gas analyzer designed for concurrently measuring the concentration of several components within a gas sample and more particularly the invention relates to a nondispersive infrared gas analyzer which is basically comprised of an arrangement that includes a source of infrared radiation, a modulator, a sample and a reference chamber, a pneumatically operating radiation detector which includes two chambers arranged upstream and downstream with respect to each other, each chamber being traversed by radiation that has already passed the sample and the reference chambers.

Gas analysis requires the ascertainment of relatively small measuring components, and often not just one but two or more which fortunately do have not completely coincidental measuring range characteristics (absorption bands). By way of example the measurement of exhaust fumes of automobiles requires a separate determination of carbon monoxide and carbon dioxide whereby by example the fumes may contain 1% by volume of carbon monoxide and about 16% of $CO_2$. Measuring these different concentrations is made difficult by the fact that the absorption utilized as the measuring effect is basically delineated by a nonlinear function. Consequently the physical length of the sample chamber is a particular parameter that has to be considered; in fact, and in order to provide for adequate sensitivity, the length of these chambers has to be matched to the measuring task to place the range of interest in a portion of the nonlinear characteristics that is not too much curved. A residual linearization can then be provided electrically in the output circuit of the detector and in a manner known per se, using nonlinearly operating and operated electronics component and auxiliary devices.

It follows from the foregoing that the measuring equipment has to be adapted physically to the measuring task which means that for different tasks different gas components one needs different constructions in the gas analyzer or one has to measure the components individually, and still use as many, differently constructed devices and gas analyzers as there are different components to be ascertained. Obviously this is an extensive way to proceed and owing to the multiplicity of functions failure rates or lack of availability of one or the other type is a nonnegligible possibility (see here e.g. German Patent 3,243,301).

DESCRIPTION OF THE INVENTION

It is an object of the present invention to provide a new and improved nondispersive infrared gas analyzer for the concurrent measurements in the concentration of several components within a gas sample; it is a more particular object of the present invention to improve nondispersive infrared gas analyzers for multiple measuring tasks that include an infrared radiation source and modulation, two juxtaposed chambers, one to serve as a measuring chamber, the other as a reference chamber, and a detection device generally which includes a pair of detection chambers being arranged one behind the other as seen in the direction of the radiation, both being traversed by radiation which in turn has respectively traversed the measuring chamber and the reference chamber and wherein these detection chambers contain gas of the kind of one of the components to be ascertained.

The objects of the invention are attained and particularly the particular object is attained through the following improvement. A second radiation detector is provided quite similar to the one mentioned earlier having also two chambers arranged, or downstream from the other and the second detection device as a whole is arranged downstream from the first mentioned radiation detector, the chambers of this second detector are filled with a second component to be detected and in between the two detector devices a filter is included having a transparency for radiation particularly within the range of a weaker absorption band of the second component, while excluding a major absorption band of that second component.

It can thus be seen that the invention is related to the improvement of gas analyzers of a construction that is known and is designed and used for the detection of one particular gas component. The measuring and reference chambers are equally long and e.g. optimized for the detection of the first component. This means that their dimensions may be "wrong" for optimizing the detection of the second component, but by limiting the detection effect, through filtering to minor absorption bands of that second component, this deficiency is cured.

For example, for the detection of carbon monoxide and carbon dioxide one will use a 20 mm long chambers, matching the detection to the 1% by volume of CO as the first component. The device that is being improved is basically a prior art device that is complete in a self contained manner for the detection of CO. Now the inventive improvement provides for features in that this known gas analyzer is supplemented so that one can also measure $CO_2$ in the sample. Here then one is cognizant of the fact that concentration of carbon dioxide is in a higher range i.e. in the 16% range. It is an inventive principle that one does not change the measuring chambers which we assumed to be adapted primarily for the CO measurement but one uses the same arrangement also for $CO_2$ detection. Owing to the fact that basically similar principles were used without adding physical and electronic function groups the range of utilization and employability of the basic system is increased.

The selectivity of measurement obtains through the chambers of the two detection systems, one being filled with the one measuring component, that means CO, while the supplemental detector is basically of similar construction but has its chambers filled with a second component, namely with $CO_2$. The modification that is (or may be) needed as far as the basic system is concerned, is that the rearmost wall of the detection chamber that is part of the basic system, is not opaque but highly transparent so that in fact radiation can pass through first through and now the selective filter as stated and then into the chambers of the second detector. Whether or not the rear wall of the second chamber of the second detector is opaque or transparent is not important in principle but transparency is preferred to permit further supplementing and extension of the system.

The desired length in measuring and sample chambers permits at least as far as one of the components is concerned adapting the sensitivity and selection of the curvature in the output characteristics so that the conventional way of linearization obtains. That however is true only as far as CO i.e. the basic or first component is concerned for which the particular system is designed. It is not true as far as the second component, and in the particular case envisioned here namely the detection of $CO_2$, the sample chambers are certainly too long. That means that the measuring characteristics as far as $CO_2$ is concerned is unfavorable and a linearization is not really feasible without excessive complications.

Aside from the fact that the cuvettes and measuring chambers are too long there is a larger overall extinction (absorption) of $CO_2$ as compared with CO in the median infrared range which is attributable to particularly strong absorption bands within the spectrum. This then is the purpose of the filter which is interposed between the two chambers which in the case of $CO_2$ prevents radiation from passing in the $CO_2$ detector having the excessive high extinction. In this particular case the 4.2 micrometer band is eliminated by this filter. The remaining absorption bands for $CO_2$ namely the 2.6 micrometer and the 2.0 micrometer band are quite adequate for the particular chosen measuring task even if the length of 20 mm of the measuring and sample chambers is too long to obtain per se an adequate measuring effect, but now this residually used characteristics is easily linearizable. The particular adaptation of equipment to specific measuring task may obtain through the selection of an appropriate filter that eliminates the difficult-to-linearize band portions.

Depending on the measuring task of course one can add components in a similar way i.e. a third detector of similar construction can be placed downstream from the second one and another filter is interposed and so forth. There is simply a practical limitation as extensive filtering finally will pose problems as far as the yield and accuracy is concerned.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Figure 1:
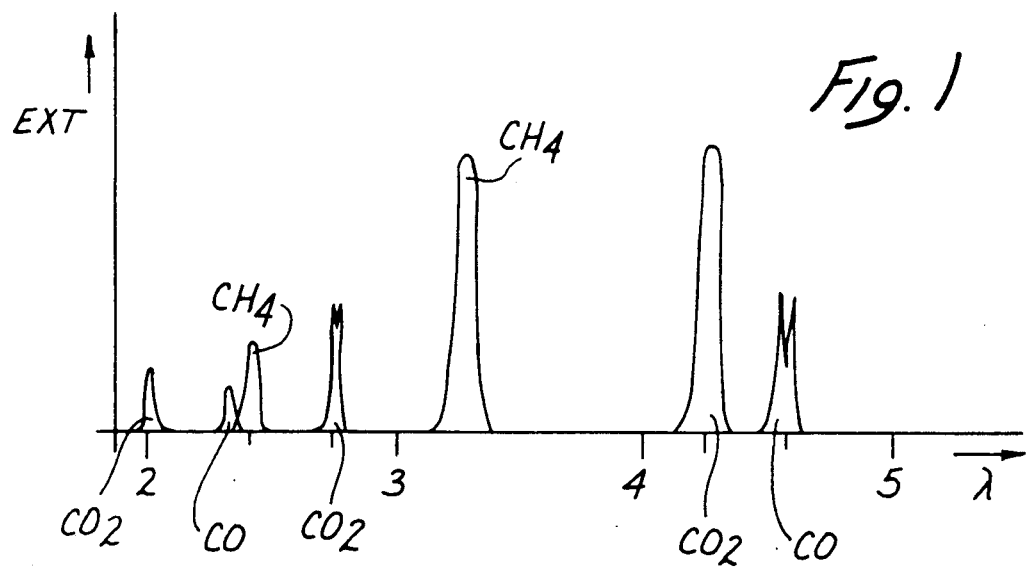
FIG. 1 illustrates a diagram of the spectral distribution of various absorption bands for CO, $CO_2$ and $CH_4$ with the respective absorption (extinction) of the median infrared light that covers from about 2 to about 5 micrometers, plotted against wavelength lambda.

Proceeding now to the detailed description of the drawings, reference is first made to FIG. 1 which shows the various bands of CO, $CO_2$ and $CH_4$. It will be explained more fully with reference to the construction for the CO, $CO_2$ and $CH_4$ detection, that a filter to be interposed in the detectors will eliminate the particular high extinction of the $CO_2$ in the 4.2 micrometer band so that the detection of $CO_2$ is limited to the two secondary bands around 2 micrometers and around 2.6 micrometers. For $CH_4$ detection, the large band in the 3.2 micrometer band is eliminated and only the one band of 2.5 micrometers is used.

Figure 2:
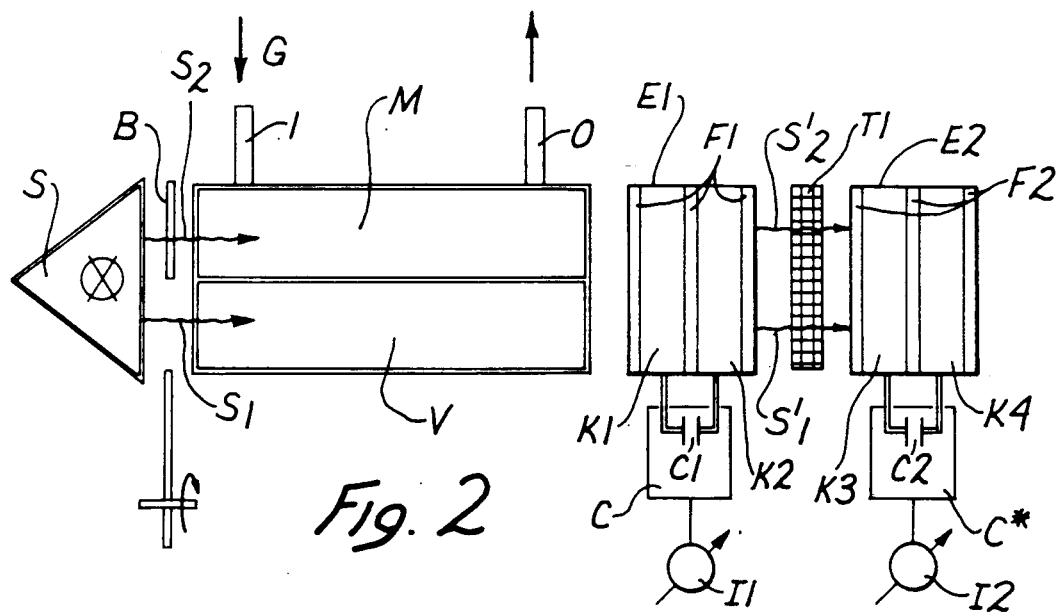
FIG. 2 is somewhat schematic view of a nondispersive infrared gas analyzer for measuring two components in a gas sample and being constructed in accordance with the preferred embodiment of the present invention.
Figure 3:
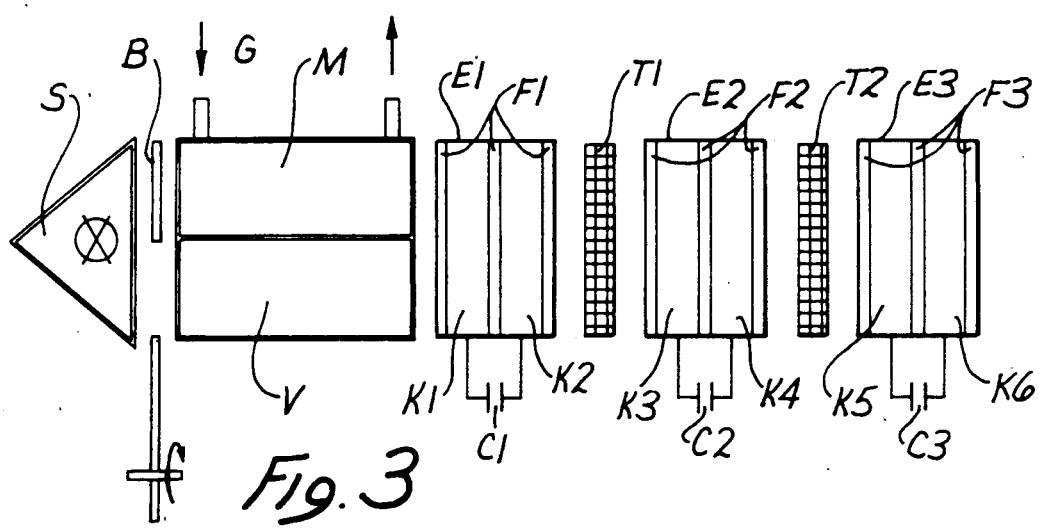
FIG. 3 is a gas analyzer analogous to FIG. 2 but designed and supplemented for measuring three components.

As far as the equipment is concerned, the nondispersive infrared gas analyzer as shown in FIG. 2 and also in FIG. 3 includes a source of radiation S with two output beams S1 and S2 there being a modulating chopper wheel B interposed; the wheel is motor driven and provides adequate modulation of the two beams S1 and S2 in a manner which is known per se. The two beam paths continue respectively in and through a reference gas chamber V, and in and through a measuring gas chamber M of equal length and usually of equal volume. They are respectively passed by the two beams which are subject to absorption. I and O are respectively inlet and outlet of measuring chamber M for the gas sample G.

Downstream from the chamber assembly V and M is arranged a first radiation detector E1 which includes a membrane capacitor C1 interconnecting an upstream or front detection chamber K1 and a downstream or rear detection chamber K2 of this detector E1. The chambers K1 and K2 are filled with one of the components to be detected, which is carbon monoxide. The two chambers K1 and K2 are both gas/pressure conductively connected to opposite sides of a membrane capacitor C1, the membrane of which will be deflected on account of pressure differences in the two chambers K1 and K2.

The chambers K1 and K2 are of course traversed by radiation that comes from B as well as from M. The detector, taken as a unit has three windows F1, a front window, a partitioning window and a rear window. Windows F1 are highly permeable to infrared radiation and should not provide for any filtration.

It can thus be seen that the detector E1 determines the concentration of CO in the gas sample G. The amount of CO contained in detector chambers K1 and K2 will be heated through the absorption but since the intensity of the two beams S1 and S2 differ owing to the selective absorption as provided by the chambers M and V, the pressure in chamber K1 will change as compared with the pressure in the chamber K2. This pressure differential is detected by the membrane capacitor C1. As far as electric circuitry is concerned capacitor C is included in a measuring circuit C and the variation in the capacitance resulting from pressure differential in chambers K1 and K2 is an electric quantity that represents the CO concentration in the gas sample G. This is indicated in a suitable instrument I1.

Thus far the arrangement is of a conventional nature except that it is absolutely necessary that there be a rear window in the detector E1 so that radiation can pass out of the chamber E1. Consequently the residual radiation S1' and S2' is passed towards a second detector E2 which is basically of the same construction as the detector E1 and has also three transparent windows F2; an upstream chamber K3 and a downstream chamber K4, these chambers are interconnected separately to opposite sides of another membrane capacitor, C2, which is part of another circuit C*; all this is quite similar to the construction of detector E1. The similarity is not a matter of necessity but of desirability and practicality as to commonality of compounds and low inventory variability. The only difference is that the chamber K3 and K4 are now filled with $CO_2$.

In between the two detectors E1 and E2 is included a filter T1, the filter is transparent for radiation which does include at least, namely a primary one absorption band of the $CO_2$ spectrum. In other words the strongest absorption as far as $CO_2$ is concerned is excluded. Looking at FIG. 1 it can be seen that it is the band around 4.2 micrometer that is by far the strongest absorption band of $CO_2$ and the principal task of the filter T1 is to eliminate that component entirely from reaching $CO_2$ detector E2 so that it does not contribute and participate in the measuring effect as provided by the detector E2. However, the filter must be transparent for at least one of the other (secondary) $CO_2$ absorption bands e.g. at least for the one which is in the 2.6 micrometer range. It may well be convenient and practical to provide the filter T1 as an interference filter with a light transmission characteristics at the 2.6 micrometer band.

Under these conditions the detector E2 is well suitable for measuring the $CO_2$ content in the gas sample G. The pressure differential that obtains by the selective absorption in the chambers K3 and K4 is detected by the membrane capacitor C2 which, as stated, is also a component in another measuring circuit C* including an amplifier that provides a proper output that is indicative of the $CO_2$ content by means of instrument 12. The selective filtering has in effect the task of compensating for the "incorrect" length of the measuring chambers M and V as far as $CO_2$ measurement is concerned.

FIG. 3 illustrates a nondispersive infrared gas analyzer which is in effect an expansion of the device shown in FIG. 2. It includes all of the elements described thus far as far as FIG. 2 is concerned and that may well include all the details i.e. the design of the equipment and of adaptation of CO and $CO_2$ measurement. FIG. 3 simply shows a device by means of which a third component that may be included in the sample G can be detected. This then is the purpose of the third radiation receiver E3.

While only a matter of convenience the following description is not intended to be restrictive but it is simply convenient to assume that E1 and E2 provide for CO and $CO_2$ detection respectively and now the detector E3 is provided to measure a third component e.g. $CH_4$. The rear wall of the chamber E2 is for reasons mentioned above transparent and the purpose is easily discernible. One simply wants to provide the system with a capability of being adaptible to further expansion.

In between the detectors E2 and E3 is provided another filter T2 which must be transparent for some portion of the radiation for which also transparency is provided by the filter T1. The particular example then will require a transparency of the 2.5 micrometer band which exhibits a significant but decidedly secondary $CH_4$ absorption. The most important aspect is that the filter T2 eliminates the strong and primary absorption band for $CH_4$.

The device is clearly capable, still under utilization of one and the same measuring and reference chamber arrangement M and V, being optimized towards measuring only one of the three components, for employing supplemental downstream detectors which permit the measurement of further components. In this case the basic design is for measuring the CO concentration and the two supplemental detectors respectively detect the $CO_2$ and $CH_4$ content.

The invention is therefore not restricted to the specific example above. First of all additional components may be detected through the adding of further radiation receivers with the yield being only the practical limitation simply because with one filter such as T1 and T2 etc after another more and more portions of the radiation are totally excluded and there may well be overlap or a weakening to such an extent that there is no more yield established. As a matter of practicality, one will detect the weakest component first and higher concentrations can be assigned to the detection of downstream detectors so as to offset the serially effective filtering.

The invention is not limited to the embodiments described above but all changes and modifications thereof, not constituting departures from the spirit and scope of the invention, are intended to be included.

I claim:

1. Nondispersive infrared gas analyzer for the concurrent measurement in the concentration of several components contained in a gas sample, the analyzer including a source of infrared radiation with two output beams in two respective beam paths;
   a modulator for modulating the two output beams;
   a measuring and sample chamber, and a reference chamber respectively included in the beam paths and being respectively traversed by said beams;
   a first pneumatic radiation detector having a front and a rear chamber both filled with one of the components and with a transparent window in between, also having a front transparent window facing both oncoming radiation beams that respectively have traversed the measuring and sample chambers, further having means connected to the two chambers for measuring the pressure differential between them, the improvement comprising:
   a second pneumatic radiation detector essentially similar to the first radiation detector having a front and a rear chamber, the front chamber having a transparent window facing radiation that has traversed the first radiation detector, there being a transparent partition between the two chambers of the second radiation detector, there further being pressure differential measuring means connected to the two chambers of the second radiation detector;
   a particular gas filling in said chambers of the second radiation detector for being the same or optically similar to a second component in the sample gas to be measured; and
   a filter disposed downstream from the first detector but upstream from the second detector and having an opaque range which covers at least a major absorption band of said second component but having a region of transparency which includes at least one secondary absorption band of said second component.

2. Nondispersive infrared gas analyzer as in claim 1 including a third detector similarly constructed as the second detector but having its chambers filled with a third component to be detected; and
   a filter upstream from the third detector eliminating another major absorption band of the third component but having a region of transparency that includes a secondary absorption band for the third component within the filter range of the first filter that eliminates the major absorption of the second component.

3. Nondispersive infrared gas analyzer as in claim 1, said filter being an interference filter.

4. Nondispersive infrared gas analyzer as in claim 2, said filters being interference filters.

* * * * *